United States Patent [19]

Wohlgemuth

[11] Patent Number: 4,713,962

[45] Date of Patent: Dec. 22, 1987

[54] TEST DEVICE FOR A DENTAL PERCUSSION INSTRUMENT

[75] Inventor: Juergen Wohlgemuth, Darmstadt, Fed. Rep. of Germany

[73] Assignee: Siemens Aktiengesellschaft, Berlin and Munich, Fed. Rep. of Germany

[21] Appl. No.: 802,255

[22] Filed: Nov. 27, 1985

[30] Foreign Application Priority Data

Dec. 13, 1984 [DE] Fed. Rep. of Germany ....... 3445507

[51] Int. Cl.⁴ .............................................. G01L 5/00
[52] U.S. Cl. ...................................................... 73/11
[58] Field of Search ......................... 73/1 R, 1 DV, 11

[56] References Cited

U.S. PATENT DOCUMENTS 1,561,154 11/1925 Gilman ..................................... 73/11
2,047,193 7/1936 Currier .................................... 73/11
4,235,094 11/1980 Matochkin et al. ..................... 73/11
4,499,906 2/1985 Wohlgemuth et al. .

FOREIGN PATENT DOCUMENTS 1016709 5/1983 U.S.S.R. ................................... 73/11

Primary Examiner—Charles A. Ruehl
Attorney, Agent, or Firm—Hill, Van Santen, Steadman & Simpson

[57] ABSTRACT

A test device for dental instruments, which have a movably seated ram that moves toward the test subject in free flight with constant speed and after impact against the subject will return to initial position, characterized by a test member which is situated externally of the instrument and has a seating surface for engagement by the ram and an arrangement for positioning the test member on a carrier member so that it would have the elasto-mechanical properties which correspond to those of a test subject. The device includes the carrier member being a cap having the test element held by a resilient material in the cap so that the cap can be inserted onto the end of the instrument. The test element can also be a resilient tongue on the carrier member, which can have a plurality of resilient tongues forming a plurality of test members. In another embodiment, the carrier member has a slot so that the test element or member is a component part separated by the slot from the remainder of the solid body of the carrier member.

12 Claims, 5 Drawing Figures

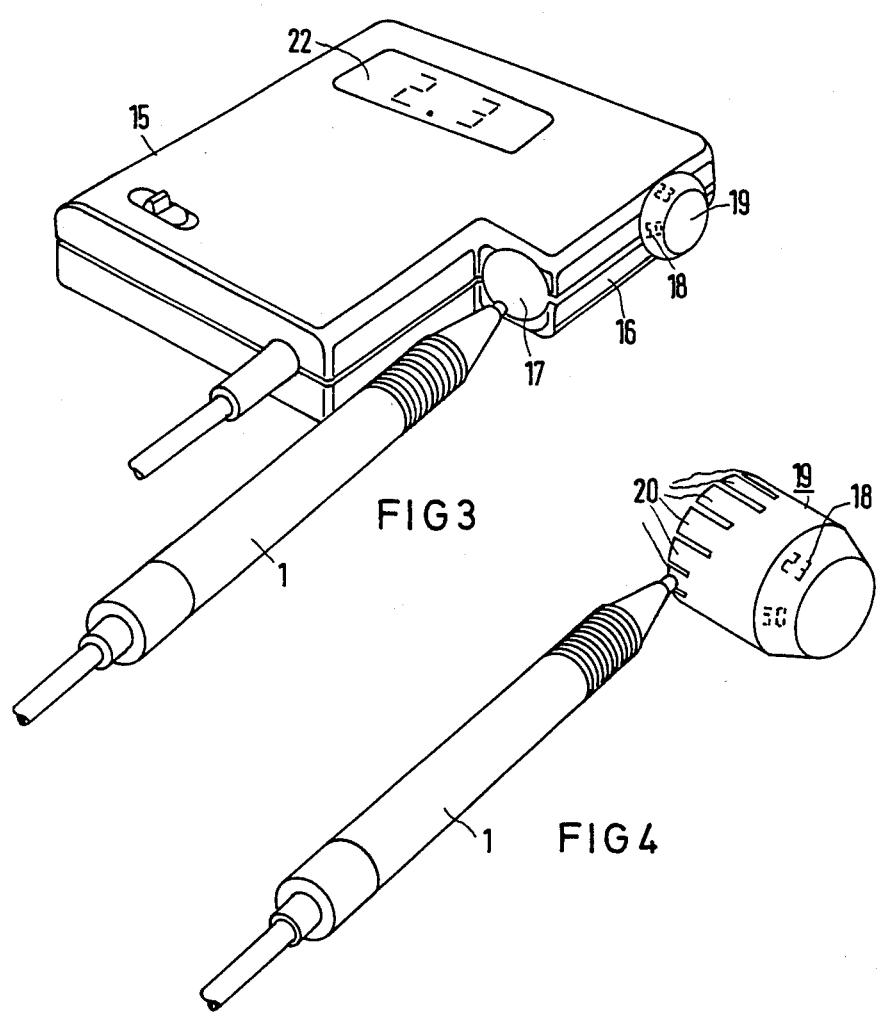
FIG 3
FIG 4
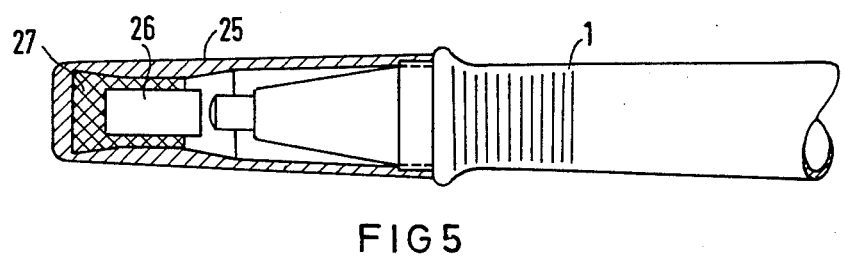
FIG 5

TEST DEVICE FOR A DENTAL PERCUSSION INSTRUMENT

BACKGROUND OF THE INVENTION

The present invention is directed to a test device for a dental percussion instrument.

A dental percussion instrument contains a movably seated ram, which is accelerated to a defined speed with the assistance of a preferably magnetic drive which is controlled by an electrnic control unit and subsequently moves toward a test subject in free flight with a speed which remains constant and the ram is then returned to its initial position by the drive after impact of the end of the ram against the subject. Percussion instruments of this type are preferably used to determine the degree of looseness of teeth in the human paradentium. An example of such a percussion instrument is disclosed in U.S. Pat. No. 4,499,906 whose disclosure is incorporated by reference thereto.

In the use of such an instrument and due to defects of the instrument or in the electronics, a faulty measurement will be obtained without this being perceived or known to the user of the instrument.

SUMMARY OF THE INVENTION

The present invention is directed to a test device which can test the function of the complete percussion apparatus or instrument before the actual measurement or testing of a patient and easily identify or determine potential defects of the instrument or of the electronics associated therewith. To accomplish these goals, the test device includes a test member, which is situated externally of the instrument and comprises a seating surface for a end of the ram to strike against, and means for mounting the test member, so it has elasto-mechanical properties corresponding to those of the test subject.

Advantages and other objects of the present invention will be readily apparent from the following description of the preferred embodiments and the accompanying drawings.

BRIEF DESCRIPTION OF THE DRAWINGS

FIG. 3 is a perspective view of another embodiment of a test drive for a percussion instrument in accordance with the present invention;

FIG. 4 is an enlarged perspective view of the percussion instrument and a part of the test device of FIG. 3; and FIG. 5 is a longitudinal cross-sectional view with portions in elevation of another embodiment of a test device for a percussion instrument in accordance with the present invention.

DESCRIPTION OF THE PREFERRED EMBODIMENTS

Figure 1:
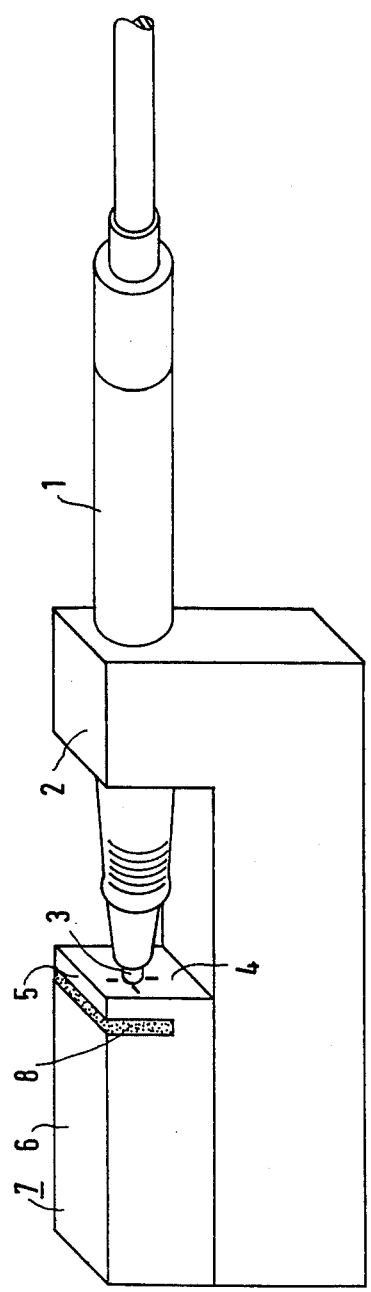
FIG. 1 is a perspective view of a test device in accordance with the present invention for a percussion instrument.

The principles of the present invention are particularly useful in a test device for a percussion instrument 1 in each of the Figures. The percussion instrument 1 has a structure which is disclosed, for example, in U.S. Pat. No. 4,499,906 which is incorporated by reference thereto. In the test device illustrated in FIG. 1, the instrument 1 is clamped in a support member or portion 2 which forms means for supporting the instrument 1 on its axis so that the end of a ram 3 of the instrument 1 can be seated against a vertical surface 4 of a test member 5 for a test procedure. The test member 5 is connected to a solid carrier member 6 and separated therefrom by a transverse slot 8. In comparison to the solid carrier member 6, the test member 5 has a certain elasticity which corresponds to that of a subject to be tested which in the present case is the elasticity of a tooth anchored in a healthy dental bed or paradentium. The test member 5 thus has defined constant elasto-mechanical properties which correspond to those of a healthy tooth in a healthy paradentium.

In the illustrated embodiment, this elasticity is achieved by utilizing a cuboid base member 7 of hard rubber, hard fabric or some other material which is suitable for this purpose. The transverse slot 8 divides the member into a solid or rigid portion or carrier member 6 and the test member 5 which is resilient in comparison thereto. In order to achieve a certain dampening of the test member 5, the slot 8 is advantageously filled with a suitable dampening material of soft rubber, foam plastic or similar materials. In the illustrated embodiment, the test member 5 and the carrier member 6 together with an instrument support portion 2 form a structural unit. Although this is advantageous it is not absolutely necessary as shown for the embodiments illustrated such as in FIG. 2. The elasto-mechanically situated test member can have various designs and be disposed in various positions.

Figure 2:
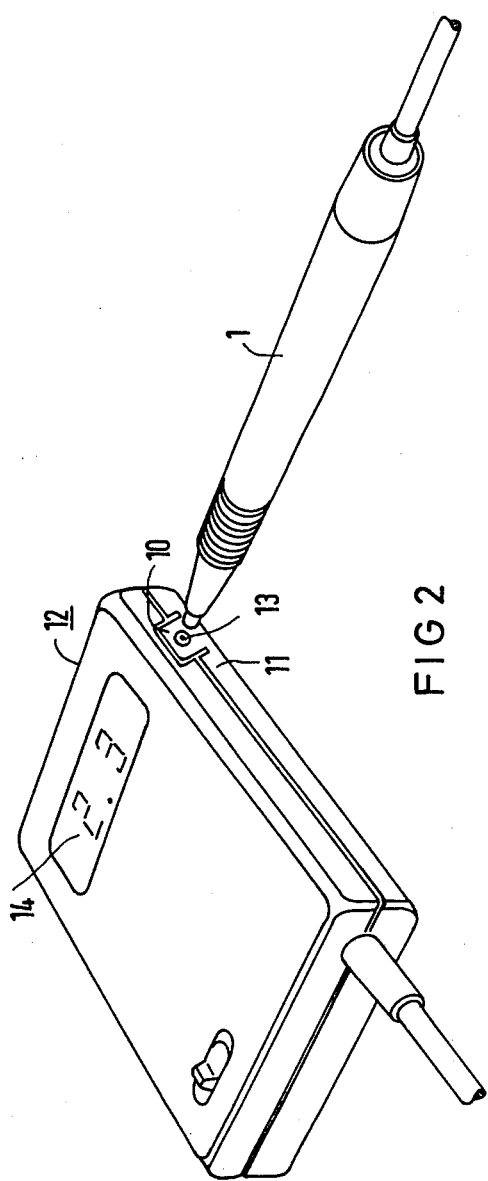
FIG. 2 is a perspective view of an embodiment or modification of the structure of a test instrument or device of the present invention.

In the embodiment illustrated in FIG. 2, the test member is a resilient tongue 10, which is partially cut from a portion of a horizontal wall 11 of a housing 12 for the percussion instrument. The tongue 10 has the above-mentioned elastic properties in comparison to the rest of the housing surface. It is expedient to provide the resilient tongue 10 with a marking or symbol 13 on which the tip of the ram of the instrument 1 is applied for the test procedure.

It is particularly advantageous to integrate the test member and the resilient tongue in the exemplary embodiment of FIG. 2 in the housing 12 in which the control and evaluation electronics for the instrument as well as a display 14 indicating the test values are provided. The test measurements can thus be read at the display and checked with a specific value defining the device function.

Instead of the partial cutting of a specific portion of a wall of the housing, a surface having a constant material weakening or material thickening in comparison to the rest of the housing wall can also be provided as a defined location of the housing. This surface must then likewise have the abovementioned elasto-mechanical properties.

In another embodiment of the test device (see FIGS. 3 and 4) which is similar to that of FIG. 1, has an instrument support mount. Over and above this, this test device comprises a multitude of test members adjustable to different values. Here the instrument support is integrated into a housing 15 and is fashioned as a sleeve-shaped longitudinally slotted part 16 which has a receptacle opening or socket 17 for receiving the end of the instrument 1. A part 19, which is provided with a scale 18, is rotatably seated at right angles to the receptacle opening or socket 17 for the instrument and this part is best illustrated in FIG. 4. The part 19 is composed a thin sleeve, which is open at one end and closed at the other end. At the open end the part 19 has a plurality of longitudinally or axially extending slots that form a plurality of resilient tongues 20 of different lengths, which slots are spaced around the circumference of the sleeve. At the closed other end the part 19 has a scale with a marking allocated to each of the tongues 20 to indicate its particular test value. By turning the sleeve or part 19 in its mounting, the individual test values can be set and when the instrument and electronics function faultlessly, they must then be displayed on the valve of the selected tongue on display 22.

Instead of providing the sleeve 19, a longitudinal displaceable carrier part having a plurality of resilient tongues of different degrees of resiliency can be provided.

Another embodiment of a test device is illustrated in FIG. 5 and is designed as an end cap 25 which is designed to surround the end of the ram in a protective fashion as it is slipped onto the end of the instrument 1. The cap 25 has a member 26 having a mass corresponding to the test subject, for example, a tooth. The member 26 is embedded in an elastic mount 27 on the inside of the sleeve-like cap 25. As previously shown in the exemplary embodiments already explained, the mount 27 has dampening and spring-like properties corresponding to those of the test subject and will provide a particular reading when the end of the ram strikes the member 26.

Although various minor modifications may be suggested by those versed in the art, it should be understood that I wish to embody within the scope of the patent granted hereon, all such modifications as reasonably and properly come within the scope of my contribution to the art.

I claim:

1. A test device for a dental percussion instrument, which instrument contains a movably seated ram which is accelerated to a definite speed preferably with the assistance of a magnetic drive, which is electronically controlled to sequentially move the ram toward a test subject in free flight with a constant speed and after impact of the end of the ram against the test subject, the ram being returned to its initial position by the drive, said test device including a test member being situated externally of the percussion instrument and having a seating surface for the end of the ram to strike, and means for mounting said test member to have the elasto-mechanical properties corresponding to those of the test subject, said means for mounting including a carrier member of a solid body of material with a slot to form the test member as a component part of said carrier member.

2. A test device according to claim 1, wherein said slot is filled with a dampening material.

3. A test device for a dental percussion instrument which instrument contains a movably seated ram which is accelerated to a definite speed, preferably with the assistance of a magnetic drive, which is electronically controlled to sequentially move the ram toward a test subject in free flight with a constant speed and after impact of the end of the ram against the test subject, the ram being returned to its initial position by the drive, said test device including a test member being situated externally of the percussion instrument and having a seating surface for the end of the ram to strike, and means for mounting said test member to have the elasto-mechanical properties corresponding to those of the test subject, said means for mounting forming the test member as a component part of a carrier member, said carrier member being a housing wall of a housing and said test member being formed in the housing wall by a material weakening of a definite portion of the housing wall.

4. A test device according to claim 3, wherein the housing contains evaluation electronics for the instrument and a display.

5. A test device for a dental percussion instrument, which instrument contains a movably seated ram which is accelerated to a definiate speed preferably with the assistance of a magnetic drive, which is electronically controlled to sequentially move the ram toward a test subject in free flight with a constant speed and after impact of the end of the ram against the test subject, the ram being returned to its initial position by the drive, said test device including a test member being situated externally of the percussion instrument and having a seating surface for the end of the ram to strike, and means for mounting said test member to have the elasto-mechanical properties corresponding to those of the test subject, said means for mounting including a carrier member having a resilient tongue extending therefrom as a component part to form the test member.

6. A test according to claim 5, wherein the resilient tongue is separated from the carrier member by a partial cut.

7. A test device according to claim 6, wherein said carrier member is a wall of a housing which contains evaluation electronics for the instrument and a display.

8. A test device for a dental percussion instrument, which instrument contains a movably seated ram which is accelerated to a definite speed preferably with the assistance of a magnetic drive, which is electronically controlled to sequentially move the ram toward a test subject in free flight with a constant speed and after impact of the end of the ram against the test subject, the ram being returned to its initial position by the drive, said test device including a common carrier member, a plurality of test members, each test member being situated externally of the percussion instrument and having a seating surface for the end of the ram to strike, and means for mounting each of said test members to have the elasto-mechanical properties corresponding to those of the test subject, said means for mounting positioning the plurality of test members on the common carrier with each of the test members having a different elasto-mechanical property.

9. A test device according to claim 8, which includes means for supporting the end of the ram of the instrument in a selected position and said means for mounting the test members being adjustable to enable selectively presenting individual test members in alignment with the end of the ram of the instrument held in the means for supporting the instrument.

10. A test device according to claim 9, wherein the common carrier is a sleeve member and the means for mounting supports the sleeve for rotation on a sleeve axis, said sleeve having a plurality of axially slots of different lengths to form a plurality of tongues having different lengths so that each tongue has a different elasto-mechanical property and by positioning different tongues for contact with the end of the ram, different values can be provided.

11. A test device according to claim 10, wherein said means for mounting positions said sleeve to rotate on an axis extending at right angles to an axis of a ram of an instrument being held by the means for supporting.

12. A test device for a dental percussion instrument, which instrument contains a movably seated ram which is accelerated to a definite speed preferably with the assistance of a magnetic drvie, which is electronically controlled to sequentially move the ram toward a test subject in free flight with a constant speed and after impact of the end of the ram against the test subject, the ram being returned to its initial position by the drive, said test device including a test member being situated externally of the percussion instrument and having a seating surface for the end of the ram to strike, and means for mounting said test member to have the elasto-mechanical properties corresponding to those of the test subject, said means for mounting including an end cap for insertion on the end of the instrument, said end cap having an interior and means for frictionally engaging said end and said test member being mounted in the interior of the cap by a resilient material.

* * * * *